United States Patent [19]
Zdarsky

[11] Patent Number: 5,533,897
[45] Date of Patent: Jul. 9, 1996

[54] INSTRUMENT FOR PREPARING THE ROOT-CANAL

[75] Inventor: Edward Zdarsky, Palm Beach, Fla.

[73] Assignee: Vereinigte Dentalwerke Antaeos Beutelrock Zipperer Zdarsky Ehrler, Munich, Germany

[21] Appl. No.: 243,484

[22] Filed: May 13, 1994

[51] Int. Cl.⁶ ............................................. A61C 5/02
[52] U.S. Cl. ............................................. 433/102
[58] Field of Search ............................. 433/102, 141, 433/224, 143, 147, 75, 144, 164; 40/913; 16/110 R, DIG. 12, DIG. 18, DIG. 19; 81/489, 177.1

[56] References Cited

U.S. PATENT DOCUMENTS 4,165,562  8/1979  Sarfatti ............................ 433/102
4,368,251  5/1981  Takasugi et al. ..................... 433/102

FOREIGN PATENT DOCUMENTS 4138686  6/1993  Germany ........................... 433/102

Primary Examiner—Cary E. O'Connor
Attorney, Agent, or Firm—Lowe, Price, LeBlanc & Becker

[57] ABSTRACT

The invention concerns a dental root-canal preparing instrument with a grip and a tool held in the grip. The grip comprises a device indicating how often the instrument already was used. The device includes a displaceable element, such as a ring, shiftable along the grip into various discrete positions, with clearances such as annular channels being provided in axially spaced manner to receive the displaceable element. Following each use, the displaceable element is shifted ahead to another discrete position, whereby the number of uses already having taken place is indicated by the present position of the displaceable element.

4 Claims, 1 Drawing Sheet

INSTRUMENT FOR PREPARING THE ROOT-CANAL

TECHNICAL FIELD

The invention concerns an instrument fitted with a grip containing a tool for preparing a dental root-canal.

BACKGROUND ART

Root-canal preparing instruments are commercially available in the form of root-canal files, root-canal drill bits or root-canal rasps and are used to widen a root canal and to clean it.

The tool proper of such root-canal preparing instruments may assume various thicknesses, there being presently twenty one different thicknesses beginning with a tip diameter of 0.06 mm up to one of 1.4 mm.

As a rule the tool proper consists of a vacuum-molten, high-alloy chromium-nickel steel evincing high strength regarding tensive, torsional and elongation stresses and required to be such that tools with initial dimensions of 0.06 mm can be manufactured.

In use, that is when such an instrument is operated by the dentist to widen or clean a root canal, said instrument is subjected to compressive, torsional and bending stresses at various rates, directions of rotations and with simultaneous up-and-down motion, i.e. an axial motion.

Furthermore root-canal preparing instruments are exposed to chemical stresses on account of disinfectants and thermal loads during heat sterilization.

Such stresses applied to root-canal preparing instruments leave traces on them such as warping, twisting by excess rotation etc. Consequently the preparing instruments and in particular those with thin tools already must be discarded possibly after being used only three times but assuredly after five-fold use as otherwise there would be danger of breakage with continued use.

While in principle used instruments may be visually checked using a magnifier, such checks on the other hand will only reveal external changes, not internal structural ones arising from material fatigue.

Accordingly it would be advantageous to the dentist if he were able to discard a root-canal preparing instrument after a specific number of uses. Such a feature however requires that he should always know how often a specific root-canal preparing instrument already has been used and sterilized. Root-canal preparing instruments known heretofore do not provide this type of information.

Consequently it is an object of the invention to create a dental root-canal preparing instrument of the initially cited kind revealing how many times it already has been used.

SUMMARY OF THE INVENTION

The root-canal preparing instrument of the invention is fitted with a component displaceably mounted on the grip and which the dentist can set following each instrument use and allowing reading the number of uses from the particular component position. Thus after each use, the dentist need only shift the displaceable component by one position at the grip into the next position so that, upon counting the positions or reading corresponding markings or numerals at the positions, the number of uses shall be easily known.

BRIEF DESCRIPTION OF THE DRAWING

Especially preferred embodiment modes of the invention are elucidated below in relation to the associated drawing.

DETAILED DESCRIPTION OF THE DRAWING

Figure 1:
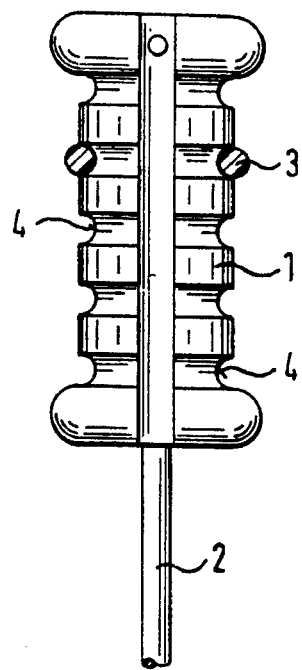
FIG. 1 is a schematic axial elevation of a first embodiment mode of the root-canal preparing instrument of the invention.

The root-canal preparing instrument shown in FIG. 1 essentially consists of a grip 1 within which is mounted the shank of the tool proper 2, for instance a file, a drill bit or a rasp.

As shown in detail in FIG. 1, annular channels 4 are present in specifically axially spaced manner in the grip 1. A ring 3 made of a preferably elastic plastic such as silicone rubber or of a fluorinated elastomer based on vinylidene-fluoride hexafluoropropylene copolymers is mounted in one of said annular channels 4, preferably in the first channel from above or below at the first use, the dimensions of the ring 3 being such that its stretchability allows displacing it axially along the grip 1 from one annular channel 4 into the next and so that it will be firmly seated in the annular channels 4.

The grip 1 also is made of plastic, the materials of the grip 1 and of the ring 3 being elected in such manner as to be chemically and thermally resistant to the sterilization stresses.

Moreover an adjusting groove running parallel to the axis may be provided in the root-canal preparing instrument shown in FIG. 1 to facilitate the axial shifting of the ring 3 from one annular channel 4 into the next. It is clear that the annular channels 4 need not run over the full periphery of the grip 1 but may assume the form of short recesses at diametrically opposite grip locations. Preferably, furthermore, the cross-section of the ring 3 shall be circular and accordingly the annular channels 4 also shall evince a partially circular cross-section as shown in FIG. 1.

Following use of the root-canal preparing instrument of FIG. 1, the dentist or his assistant can shift the ring 3 by one position into the next annular channel 4 by slightly lifting said ring, in the adjusting groove if present, before sterilization. FIG. 1 illustratively shows the root-canal preparing instrument with the ring 3 in the second annular channel 4, showing that the instrument was sterilized and is ready for the second utilization. Following the second utilization the ring 3 is displaced into the third annular channel 4.

By counting the particular position of the ring 3 or by means of corresponding colored markings or numerals at the annular channels 4, the dentist easily can read and recognize how often the instrument already was used. The number of the annular channels 4 depends on how often the instrument shall be used. If the maximum number of uses is five, five annular channels 4 shall be provided, as a result of which the dentist can discard the instrument if ring 3 is in the fifth and last annular channel 4.

Furthermore rings 3 of different colors may be used, so that, if for instance there are only five annular channels 4, the number of possible cycles of operation may be increased in that, following the first five uses, the ring 3 shall be replaced by one of another color. Illustratively the first ring may be white and be exchanged against a yellow one (in relation to the dental color scale).

Figure 2:
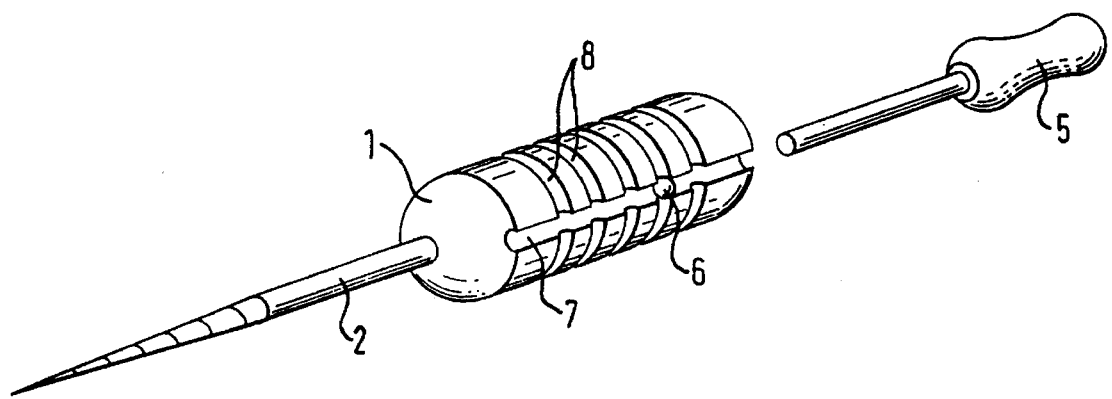
FIG. 2 is a perspective of a second embodiment mode of the root-canal preparing instrument of the invention.

FIG. 2 shows another embodiment mode of the dental root-canal preparing instrument of the invention which is fitted with a device showing any time how often the instrument already has been used. In the instrument of FIG. 2, this device consists of a displaceable and preferably spherical element 6 displaceably located in a groove 7 of the grip 1 running parallel to the axis. The cross-section of the groove 7 is such that the received element is retained therein. As regards a spherical element 6, therefore the cross-section of groove 7 is circular by an arc exceeding 180°.

Moreover a bar-shaped component 5 is provided as the adjusting means which fits into the groove 7 and which can be manually actuated to displace the element 6 along the axial groove 7.

As shown by FIG. 2, axially spaced clearances 8 run peripherally on the grip 1 and are so designed and dimensioned that the element 6 can snap into position at these sites. For this purpose the element 6 is made of a material similar to that of the ring 3 of the embodiment mode of FIG. 1.

Furthermore the clearances 8 may be such that the element 6 can be circumferentially inserted into them so it be stationary in its axial position.

The illustrative embodiment mode of FIG. 2 also is shown in a state of readiness for the second use because the element 6 is present at the second clearance. This is the state prior to the second sterilization for the second use. Following second use, the element 6 is displaced by one position into the next clearance 8, whereby it is plain that the instrument is ready for the third sterilization and the third use.

In this embodiment mode as in that of FIG. 1, the displaceable element 6 can be displaced by five positions and if more than five positions are needed, again elements 6 of different colors may be employed.

I claim:

1. A dental root-canal preparing instrument comprising a grip and a tool contained therein, and further comprising a displaceable element which can be shifted in a direction parallel to a grip axis into one of plural discrete positions on the grip, wherein the displaceable element is at least one elastic ring and further including annular channels formed in the grip at discrete positions, said at least one ring being received in said channels.

2. A dental root-canal preparing instrument comprising a grip and a tool contained therein, and further comprising a displaceable element which can be shifted in a direction parallel to a grip axis into one of plural positions on the grip, wherein the displaceable element is spherical and a guide groove extends along the grip parallel to a longitudinal axis thereof, said guide groove including, in cross-section, an arcuate groove wall subtending an arcuate interval greater than 180° to receive the spherical element in snap fitting engagement.

3. A dental root-canal preparing instrument comprising a grip and a tool contained therein, and further comprising a displaceable element which can be shifted in a direction parallel to a grip axis into one of plural discrete positions on the grip, wherein the displaceable element is present in a guide groove formed in the grip and extending parallel to the grip axis, and further including snap-in means for receiving the displaceable element at the discrete positions, further comprising a bar-shaped actuating means engageable into the guide groove to advance the displaceable element within the groove.

4. A dental root-canal preparing instrument comprising a grip and a tool contained therein, and further comprising a displaceable element which can be shifted in a direction along a grip axis into one of plural discrete positions on the grip, wherein the displaceable element is present in at least one guide groove formed on an exterior surface of the grip.

* * * * *